United States Patent [19]
Kikuchi et al.

[11] Patent Number: 5,506,230
[45] Date of Patent: Apr. 9, 1996

[54] FATTY EMULSION

[75] Inventors: Tetsuro Kikuchi; Katsura Tottori; Shinichi Ishikawa; Yoshito Masuda, all of Tokushima, Japan

[73] Assignee: Otsuka Pharmaceutical Co., Ltd., Japan

[21] Appl. No.: 156,932

[22] Filed: Nov. 24, 1993

Related U.S. Application Data

[63] Continuation of Ser. No. 781,930, Oct. 24, 1991, abandoned.

[30] Foreign Application Priority Data

Oct. 31, 1990 [JP] Japan .................................. 2-295832

[51] Int. Cl.$^6$ .............................................. A61K 31/495
[52] U.S. Cl. .............................................. 514/255; 514/938
[58] Field of Search .......................... 514/78, 255, 938

[56] References Cited

U.S. PATENT DOCUMENTS 4,895,847  1/1990  Oshiro .................................... 514/255

FOREIGN PATENT DOCUMENTS

| | | |
|---|---|---|
| 0173331 | 5/1986 | European Pat. Off. . |
| 56-70826 | 6/1981 | Japan . |
| 59-122423 | 7/1984 | Japan . |
| 62-29511 | 12/1987 | Japan . |
| 63-23811 | 2/1988 | Japan . |
| 1-226807 | 9/1989 | Japan . |
| 2-25418 | 1/1990 | Japan . |
| 2-167217 | 2/1990 | Japan . |
| 5-18806 | 3/1993 | Japan . |

OTHER PUBLICATIONS

Remmington's Pharmaceutical Sciences (1985) Mack Publishing Co. pp. 317–328.
Merck Index, p. 1376, Abst. #8685, 1989.
Unlisted Drugs, vol. 13, No. 9, p. 90 (Sep. 1961).
Unlisted Drugs, vol. 28, No. 3, p. 40, (Mar. 1976).
Svensk Farm. Tidskr., 65: p. 320, (Apr. 30, 1961).
Advanced Drug Delivery Reviews, vol. 5, pp. 189–208 (1990).

*Primary Examiner*—Raymond Henley, III

[57] ABSTRACT

Fatty emulsion containing 2,3-dihydro-1H-indene derivatives represented by the general formula (1) as an active ingredient, a pharmaceutically acceptable oily ingredient and water. Said fatty emulsion is useful for improving anoxemic and hypoxic symptoms and syndromes, so that is effectively used for preventive agent for arrythmia and heart failure caused by shortage of oxygen and the like.

20 Claims, No Drawings

FATTY EMULSION

This application is a continuation of application Ser. No. 07/781,930 filed Oct. 24, 1991, now abandoned.

DETAILED DESCRIPTION OF THE INVENTION

1. Industrial Field of Utilization

The present invention relates to a fatty emulsion.

2. Prior Art and the Problems

It is a known fact that the 2,3-dihydro-1H-indene derivatives represented by the general formula

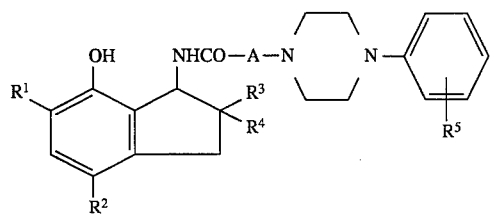

($R^1$, $R^2$, $R^3$ and $R^4$ are the same or different and are each represents lower alkyl group; $R^5$ represents a lower alkoxy group; A represents a lower alkylene group) possess excellent activities for improving anoxemic and hypoxic symptoms and syndromes and accordingly can be effectively used as improving agents for hypoxia, such as cerebral function-activating agent, curative agent for amnesia, curative agent for presbyophrenia, improving agent for respiratory arrest and hypoxia caused by poisoning with potassium cyanide, preventive agent for arrythmia and heart failure caused by shortage of oxygen, and the like [Japanese Patent Application Kokai (Laid-Open) Nos. 69747/1986 and 60610/1986, corresponding to U.S. Pat. Nos. 4,788,130 and 4,895,847 and EP-A-0173331].

Currently, the 2,3-dihydro-1H-indene derivatives are in use as peroral administration preparations (e.g. tablets, granular preparation) because the derivatives have very low solubility in water.

Meanwhile, the intravenous administration of the 2,3-dihydro-1H-indene derivatives is considered to be preferable when the oral administration to a patient in need of remedy is difficult because the patient has lost consciousness or is in a serious or critical condition or because of other reasons, or when it is desired that said derivatives exhibit the activity rapidly.

However, the conventional pharmaceutical preparations containing said derivatives allow no satisfactory intravenous administration; accordingly, the development of a pharmaceutical preparation containing said derivative, allowing improved intravenous administration, has been desired.

MEANS FOR SOLVING THE PROBLEMS

The present invention relates to a fatty emulsion containing a 2,3-dihydro-1H-indene derivative represented by the general formula (1) as an active ingredient, a pharmaceutically acceptable oily ingredient and water.

In the general formula (1), as the lower alkyl group represented by $R^1$, $R^2$, $R^3$ and $R^4$, there can be mentioned, for example, straight chain or branched chain alkyl groups having 1 to 6 carbon atoms such as methyl, ethyl, propyl, isopropyl, butyl, tert-butyl, pentyl, hexyl, 1-methylpropyl, 2-methylpropyl, 1,1-dimethylporopyl, 1-methylbutyl, 2-methylbutyl, 3-methylbutyl, 2,2-dimethylpropyl, 2,3-dimethylpropyl, 1-methylpentyl, 1,1-dimethylbutyl and 1-ethylbutyl groups and the like.

As to the lower alkoxy group represented by $R^5$, there can be mentioned, for example, straight chain or branched chain alkoxy groups having 1 to 6 carbon atoms such as methoxy, ethoxy, propoxy, isopropoxy, butoxy, tert-butoxy, pentyloxy and hexyloxy groups and the like.

As to the lower alkylene group represented by A, there can be mentioned, for example, straight chain or branched chain alkylene groups having 1 to 6 carbon atoms such as methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene groups and the like.

As to the oily ingredient used in the present invention, various conventionally known oily ingredients can be used as long as they are pharmaceutically acceptable. There can be mentioned, for example, oily ingredients derived from vegetable sources, such as soybean oil, cottonseed oil, sesame oil, corn oil, olive oil, rice bran oil, rapeseed oil, safflower oil, sunflower oil, wheat germ oil, evening primrose oil, castor oil and the like, as well as oily ingredients derived from animal sources, such as mackerel oil, sardine oil, milk fat and the like. As to the oily ingredient of the present invention, there can also be used synthesized or structured lipids such as midium-length-chain fatty acid triglyceride (MCT), long-chain fatty acid triglyceride (LCT) and the like. The amount of the oily ingredient used is not specifically restricted as long as it enables the production of the fatty emulsion of the present invention, and can be appropriately selected from a wide range. However, the amount is generally about 0.1 to 50 w/v %, preferably about 5 to 25 w/v %, based on the amount of the fatty emulsion of the present invention.

The amount of the 2,3-dihydro-1H-indene derivative of the general formula (1) as an active ingredient is generally 2 parts by weight or less, preferably about 0.01 to 1 part by weight per 100 parts by weight of the oily ingredient [part(s) by weight is hereinafter referred to merely as part(s)].

In the present invention, it is possible that an emulsifying agent, an emulsifying adjuvant, a stabilizer, an isotonic agent, a pH-controlling agent, and the like be compounded as desired into the fatty emulsion in order to make fine the oil droplet particles in the fatty emulsion or stabilize the emulsion.

The emulsifying agent is not particularly restricted as long as it is pharmaceutically acceptable. Various conventionally known emulsifying agents can be used, such as phospholipid, non-ionic surface active agent and the like. Specific examples of the phospholipid are phosphatidylcholine, phosphatidylethanolamine, phosphatidylserine, phosphatidylinositol, phosphatidylglycerol, diphosphatidylglycerol and sphingomyelin. Lecithin which is a mixture of these phospholipids, as well as hydrogenated lecithin can also be used. These phospholipids can be of any origin, and there are used, for example, those derived from vegetable sources (e.g. soybean) and those derived from animal sources, such as yolk and the like. A purified phospholipid is particularly preferable. The non-ionic surface active agent is not particularly restricted as long as it is pharmaceutically acceptable. Various conventionally known non-ionic surface active agents can be used, such as fatty acid monoglycerides, fatty acid sorbitan esters, fatty acid sugar esters, polyglycerine alkenoates, polyoxyalkylene alkyl ethers, polyoxyalkylene alkylphenyl ethers, polyoxyalkylene sorbitan fatty acid esters, polyoxyethylene sorbitol fatty acid esters, polyoxyalkylene glycerol fatty acid esters, polyoxyalkylene alkenoyl amides, polyoxyalkylene alkene amines, polyoxyalkylene castor oils, polyoxyalkylene hydrogenated castor oils, polyoxyalkylene fatty acid esters, polyoxyalkylene polyoxypropylene copolymers, their derivaties and the like. The emulsifying agent is used in an amount of generally about 1 to 50 parts, preferably about 5 to 25 parts per 100 parts of the oily ingredient.

The emulsifying adjuvant is not particularly restricted as long as it is pharmaceutically acceptable. There can be used various conventionally known emulsifying adjuvants, for example, a straight chain or branched chain fatty acid having 6 to 22 carbon atoms (preferably a straight chain fatty acid having 12 to 20 carbon atoms) or a salt thereof. Preferable examples of the fatty acid are stearic acid, oleic acid, linoleic acid, linolenic acid and palmitic acid. The salt of the fatty acid include physiologically acceptable salts, for example, alkali metal salts (e.g. sodium salt, potassium salt) and alkaline earth metal salts (e.g. calcium salt).

The stabilizer is not particularly restricted as long as it is pharmaceutically acceptable. Various conventionally known stabilizers can be used, such as tocopherol, ascorbic acid, EDTA, butylhydroxyanisole, butylhydroxytoluene and the like (these are used to allow the resulting fatty emulsion to have an antioxidative activity) and parahydroxyalkylbenzoates, sorbic acid, salicylic acid and salts thereof, phenol, cresol and the like (these are used to allow the resulting fatty emulsion to have an antiseptic activity).

The isotonic agent is not particularly restricted as long as it is pharmaceutically acceptable. Various conventionally known isotonic agents can be used, such as glycerol, glucose, mannitol, sorbitol, fructose, xylitol, sucrose, lactose, maltose and the like.

The pH-controlling agent is not particularly restricted as long as it is phamaceutically acceptable and can control the pH of the fatty emulsion of the present invention at about pH 2 to 11, preferably about pH 5 to 9. Various conventionally known pH-controlling agents can be used, such as sodium hydroxide, sodium carbonate, sodium hydrogencarbonate, hydrochloric acid and the like.

The particle size of the particles being dispersed in the fatty emulsion of the present invention are not particularly restricted, and desirably are generally 7 μm or less, preferably 2 μm or less.

In producing the fatty emulsion of the present invention, firstly a 2,3-dihydro-1H-indene derivative represented by the general formula (1) is mixed with a pharmaceutically acceptable oily ingredient and the resulting mixture is heated as necessary to obtain a uniform solution. Thereto are added water and, as necessary, an emulsifying agent, an emulsifying adjuvant, a stabilizer, an isotonic agent, a pH-controlling agent, etc., followed by stirring, whereby a crude emulsion is prepared. Then, a necessary amount of water is added to the crude emulsion and the mixture is completely emulsified using a conventional homogenizer (e.g. pressure injection type homogenizer, ultrasonic homogenizer or the like). The resulting emulsion is filtered and poured into a container (e.g. ampule or vial). The filled container is sealed and sterilized.

The administration method of the fatty emulsion of the present invention is not particularly restricted, and the fatty emulsion of the present invention can be administered by various methods which differ depending upon the type of preparation, the age, sex and other conditions of patient, the condition of disease, etc., and the fatty emulsion is generally administered intravenously. As a matter of course, the fatty emulsion may be administered orally.

The dose of the pharmaceutical composition of the present invention is appropriately selected depending upon the type and administration method of composition, the age, sex and other conditions of patient, the condition of disease, etc. It is desirable that the dose may be generally about 0.001 to 100 mg [in terms of the amount of the compound of the general formula (1), i.e. the amount of the active ingredient] per day per kg of body weight. The pharmaceutical composition can be separately administered in 2 to 4 times a day.

EFFECTS OF THE INVENTION

The fatty emulsion of the present invention is an excellent preparation for intravenous administration which can be used when the rapid exhibition of pharmacological activity is desired. It can be used also as an oral preparation. Moreover, the fatty emulsion of the present invention, as compared with the conventional preparations of similar type, has a high speed in intracephalic movement, is resistant to being inactivated in a living body, can be easily taken into phagocytes, etc. and distributed into malady sites, in particular, and accordingly can be efficiently accumulated in lesion sites. Thus, the fatty emulsion of the present invention can exhibit remarkably high efficacy as compared with conventional pharmaceutical preparations of similar type.

EXAMPLES

The preparation examples and pharmacological tests of the fatty emulsion of the present invention are shown below.

Preparation Example 1

| | |
|---|---|
| 1-[4-(3-Methoxyphenyl)-1-piperazinyl]-acetylamino-2,3-dihydro-7-hydroxy-2,2,4,6-tetramethyl-1H-indene | 0.06 g |
| Soybean oil | 20.00 g |
| Yolk lecithin | 1.20 g |
| Glycerol | 2.25 g |
| Sodium hydroxide | Sufficient quantity |
| Water for injection | Sufficient quantity |
| | 100 ml |

The above active ingredient compound was dissolved in soybean oil, which was heated to about 70° to 80° C., to obtain an oil phase. Glycerol was dissolved in water for injection, and the solution was heated to about 70° to 80° C. To the solution was added yolk lecithin, and the mixture was thoroughly stirred by use of a homomixer to make the mixture into dispersion to obtain an aqueous phase. The aqueous phase was mixed with the previously prepared oil phase, and the mixture was emulsified at about 70° to 80° C. by use of a homomixer to obtain a crude emulsion. The crude emulsion was further emulsified by a pressure injection type homogenizer (manufactured by APV Gaulin, Inc.) to obtain an emulsion having particle diameters of 1 μm or less. The emulsion was filtered through a filter of 0.8 to 1.2 μm and poured into vials. The vials were sterilized by high pressure steam at 121° C. for 20 minutes to obtain a fatty emulsion of the present invention.

Preparation Example 2

| | |
|---|---|
| 1-[4-(3-Methoxyphenyl)-1-piperazinyl]-acetylamino-2,3-dihydro-7-hydroxy-2,2,4,6-tetramethyl-1H-indene | 0.01 g |
| Soybean oil | 20.00 g |

-continued

| | |
|---|---|
| Yolk lecithin | 1.20 g |
| Glycerol | 2.25 g |
| Sodium hydroxide | Sufficient quantity |
| Water for injection | Sufficient quantity |
| | 100 ml |

By the same procedure as in Preparation Example 1 was repeated using the above-mentioned formulation, to obtain a fatty emulsion of the present invention.

Preparation Example 3

| | |
|---|---|
| 1-[4-(3-Methoxyphenyl)-1-piperazinyl]-acetylamino-2,3-dihydro-7-hydroxy-2,2,4,6-tetramethyl-1H-indene | 0.14 g |
| Soybean oil | 20.00 g |
| Yolk lecithin | 1.20 g |
| Glycerol | 2.25 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Preparation Example 4

| | |
|---|---|
| 1-[4-(3-Methoxyphenyl)-1-piperazinyl]-acetylamino-2,3-dihydro-7-hydroxy-2,2,4,6-tetramethyl-1H-indene | 0.03 g |
| Soybean oil | 10.00 g |
| Yolk lecithin | 1.20 g |
| Glycerol | 2.25 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Preparation Example 5

| | |
|---|---|
| 1-[4-(3-Methoxyphenyl)-1-piperazinyl]-acetylamino-2,3-dihydro-7-hydroxy-2,2,4,6-tetramethyl-1H-indene | 0.06 g |
| Soybean oil | 20.00 g |
| Hydrogenated soybean lecithin | 1.20 g |
| Mannitol | 5.00 g |
| Sodium hydrogencarbonate | 0.20 g |
| Water for injection | Sufficient quantity |
| | 100 ml |

The same procedure as in Preparation Example 1 was repeated by using the above-mentioned formulation, to obtain a fatty emulsion of the present invention.

Preparation Example 6

| | |
|---|---|
| 1-[4-(3-Methoxyphenyl)-1-piperazinyl]-acetylamino-2,3-dihydro-7-hydroxy-2,2,4,6-tetramethyl-1H-indene | 0.1 g |
| Soybean oil | 20.0 g |
| Hydrogenated soybean lecithin | 1.2 g |
| oleic acid | 0.2 g |
| Polyethylene glycol 6000 | 0.2 g |
| Mannitol | 3.5 g |
| Sodium hydrogencarbonate | 0.1 g |
| Water for injection | Sufficient quantity |
| | 100 ml |

A fatty emulsion of the present invention was obtained by using the above-mentioned formulation, in the same manner as in Preparation Example 1 except that the active ingredient compound was dissolved in soybean oil, oleic acid and polyethylene glycol 6000 to obtain an oil phase and that hydrogenated soybean lecithin, mannitol and sodium hydrogencarbonate were dissolved in water for injection to obtain an aqueous phase.

Preparation Example 7

| | |
|---|---|
| 1-[4-(3-Methoxyphenyl)-1-piperazinyl]-acetylamino-2,3-dihydro-7-hydroxy-2,2,4,6-tetramethyl-1H-indene | 0.06 g |
| Capric acid triglyceride | 20.00 g |
| Yolk lecithin | 0.8 g |
| Glycerol | 2.25 g |
| Sodium hydroxide | Sufficient quantity |
| Water for injection | Sufficient quantity |
| | 100 ml |

A fatty emulsion of the present invention was obtained by using the above-mentioned formulation, in the same manner as in Preparation Example 1 except that the active ingredient compound was dissolved in captic acid triglyceride to obtain an oil phase and that yolk lecithin, glycerol and sodium hydroxide were dissolved in water for injection to obtain an aqueous phase.

Preparation Example 8

| | |
|---|---|
| 1-[4-(3-Methoxyphenyl)-1-piperazinyl]-acetylamino-2,3-dihydro-7-hydroxy-2,2,4,6-tetramethyl-1H-indene | 0.07 g |
| Soybean oil | 20.00 g |
| Phosphatidylcholine | 1.50 g |
| Oleic acid | 1.00 g |
| Glycerol | 2.25 g |
| Sodium hydroxide | Sufficient quantity |
| Water for injection | Sufficient quantity |
| | 100 ml |

A fatty emulsion of the present invention was obtained by using the above-mentioned formulation, in the same manner as in Preparation Example 1 except that the active ingredient compound was dissolved in soybean oil and oleic acid to obtain an oil phase and that phosphatidylcholine, glycerol and sodium hydroxide were dissolved in water for injection to obtain an aqueous phase.

Preparation Example 9

| | |
|---|---|
| 1-[4-(3-Methoxyphenyl)-1-piperazinyl]-acetylamino-2,3-dihydro-7-hydroxy-2,2,4,6-tetramethyl-1H-indene | 0.3 mg |
| Soybean oil | 0.10 g |

| | |
|---|---|
| Yolk lecithin | 0.01 g |
| Glycerol | 2.25 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Preparation Example 10

| | |
|---|---|
| 1-[4-(3-Methoxyphenyl)-1-piperazinyl]-acetylamino-2,3-dihydro-7-hydroxy-2,2,4,6-tetramethyl-1H-indene | 0.01 g |
| Soybean oil | 5.00 g |
| Yolk lecithin | 0.50 g |
| Glycerol | 2.50 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Preparation Example 11

| | |
|---|---|
| 1-[4-(3-Methoxyphenyl)-1-piperazinyl]-acetylamino-2,3-dihydro-7-hydroxy-2,2,4,6-tetramethyl-1H-indene | 0.1 g |
| Soybean oil | 25.0 g |
| Yolk lecithin | 1.2 g |
| Glycerol | 2.25 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Preparation Example 12

| | |
|---|---|
| 1-[4-(3-Methoxyphenyl)-1-piperazinyl]-acetylamino-2,3-dihydro-7-hydroxy-2,2,4,6-tetramethyl-1H-indene | 0.15 g |
| Soybean oil | 50.0 g |
| Yolk lecithin | 2.4 g |
| Glycerol | 2.25 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Preparation Example 13

| | |
|---|---|
| 1-[4-(3-Methoxyphenyl)-1-piperazinyl]-acetylamino-2,3-dihydro-7-hydroxy-2,2,4,6-tetramethyl-1H-indene | 0.4 g |
| Soybean oil | 20.0 g |
| Yolk lecithin | 1.2 g |
| Glycerol | 2.25 g |
| Oleic acid | 1.00 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Preparation Example 14

| | |
|---|---|
| 1-[4-(3-Methoxyphenyl)-1-piperazinyl]-acetylamino-2,3-dihydro-7-hydroxy 2,2,4,6-tetramethyl-1H-indene | 0.2 g |
| Soybean oil | 20.0 g |
| Yolk lecithin | 1.2 g |
| Glycerol | 2.25 g |
| Oleic acid | 1.00 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Preparation Example 15

| | |
|---|---|
| 1-[4-(3-Methoxyphenyl)-1-piperazinyl]-acetylamino-2,3-dihydro-7-hydroxy-2,2,4,6-tetramethyl-1H-indene | 2.0 mg |
| Soybean oil | 20.0 g |
| Yolk lecithin | 1.2 g |
| Glycerol | 2.25 g |
| Sodium hydroxide | Sufficient quantity |
| Water for injection | Sufficient quantity |
| | 100 ml |

The same procedure as in Preparation Example 1 was repeated by using the above-mentioned formulation, to obtain a fatty emulsion of the present invention.

Pharmacological Test

This test was conducted in accordance with the method of Manaka, et al. [Nichi Saigai Shi, 25, 675–685 (1977)] and the method of Miyamoto, et al. [Life Sci., 28, 861–869 (1981)]. That is, ICR-strain male mice (Clea Japan, Inc.) were fixed at the head; an acrylic resin-made cylindrical weight (diameter: 19 mm, length: 50 mm, weight: 20 g) was dropped, in a cylindrical tube, onto the vertex of each mouse from a height of 20 cm. As a result, each mouse was seized with cramp for about 10 seconds and then lost the righting reflex; recovered the righting reflex after a little while; thereafter, crouched for a while and stopped the spontaneous movement. The time from the impact at the head to the recovery of the righting reflex (hereinafter referred to as righting reflex time, i.e. RR time) and the time from the impact at the head to the appearance of the spontaneous movement (hereinafter referred to as spontaneous movement time, i.e. SM time) were measured each as a criterion for reduction in cerebral function.

To the mice of test group was intravenously administered the fatty emulsion of Preparation Example 1 according to the present invention, at a dose of 0.0003 to 0.03 mg/kg of body weight 15 minutes before the impact at the head. To the mice of control group was intravenously administered a physiologically saline solution at a dose of 0.05 ml/10 g body weight.

In the significance test, one-way analysis of variance was conducted and then a two-tailed Dunnett's test was used. $ED_{50}$ was calculated using a profit method. The results are shown in Table 1.

TABLE 1

| Prug | Dose (mg/kg i.v.) | RR time (mean ± S.E., sec.) | SM time (mean ± S.E., sec.) | ED50 value (95% confidence limit) |
|---|---|---|---|---|
| Fatty emulsion of Preparation Example 1 | 0.0003 | 136.3 ± 9.4 | 183.8 ± 11.5 | RR time |
| | 0.001 | 113.6 ± 14.6 | 162.0 ± 19.5 | 0.005 |
| | 0.003 | 72.5 ± 14.8 | 107.7 ± 22.0 | (0.002 to 0.009) |
| | 0.01 | 37.1 ± 11.6 | 61.8 ± 15.5 | SM time |
| | 0.03 | 24.4 ± 13.2 | 47.6 ± 19.6 | 0.005 |
| | | | | (0.004 to 0.007) |
| Control (physiologicall saline solution) | 0 | 138.0 ± 6.5 | 195.0 ± 11.3 | | n = 10, **: P < 0.01 vs physiological saline solution (1-way ANOVA, two-tailed Dunnett's test)

The followings are clear from Table 1. The fatty emulsion of the present invention reduced RR time and SM time in proportion to the amount used, from 0.001 mg/kg i.v. and significantly from 0.003 mg/kg i.v. The $ED_{50}$ values for reduction in RR time and SM time were both 0.005 mg/kg i.v. Accordingly, the fatty emulsion of the present invention possesses a cerebral function-activating action, in the mice of a coma state caused by cerebral concussion.

What is claimed is:

1. An oil in water fatty emulsion comprising a 2,3-dihydro-1H-indene compound as an active ingredient having the formula

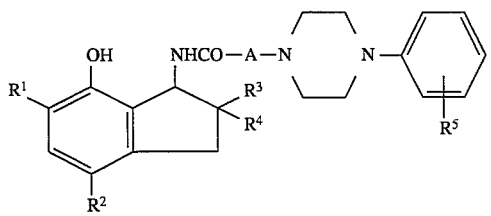

wherein $R^1$, $R^2$, $R^3$ and $R^4$ are the same or different and each is a lower alkyl group, $R^5$ is a lower alkoxy group and A is a lower alkylene group; a pharmaceutically acceptable oil; a phospholipid as an emulsifier present in said emulsion in addition to any phospholipid which may be present in said oil in an amount from 1 to 50 parts by weight per 100 parts by weight of said oil; an isotonic agent; and water.

2. The oil in water fatty emulsion of claim 1, wherein the pharmaceutically acceptable oil is an oil derived from a plant.

3. The oil in water fatty emulsion of claim 2, wherein the oil is soybean oil.

4. The oil in water fatty emulsion of claim 3, wherein the amount of the soybean oil is from 0.1 to 50 w/v % based on the amount of the fatty emulsion.

5. The oil in water fatty emulsion of claim 4, wherein the amount of the soybean oil is from 5 to 25 w/v % based on the amount of the fatty emulsion.

6. The oil in water fatty emulsion of claim 1, wherein the phospholipid is used in an amount of from 5 to 25 parts by weight per 100 parts by weight of the oil.

7. The oil in water fatty emulsion of claim 1, wherein the phospholipid is lecithin or hydrogenated lecithin.

8. The oil in water fatty emulsion of claim 7, wherein the lecithin is yolk lecithin.

9. The oil in water fatty emulsion of claim 1, wherein the isotonic agent is glycerol.

10. The oil in water fatty emulsion of claim 1, wherein the indene compound as the active ingredient is present in an amount of from 2 parts by weight or less per 100 parts by weight of the oil.

11. The oil in water fatty emulsion of claim 10, wherein the indene compound is present in an amount of from 0.01 to 1 part by weight per 100 parts by weight of the oil.

12. The oil in water fatty emulsion of claim 1, wherein the indene compound is 1-[4-(3-methoxyphenyl)-1-piperazinyl] acetylamino- 2,3-dihydro-7-hydroxy-2,2,4,6-tetramethyl-1H-indene.

13. The oil in water fatty emulsion of claim 1, containing particle size diameters of 2 μm or smaller.

14. An oil in water fatty emulsion comprising a 2,3-dihydro-1H-indene compound as an active ingredient having the formula

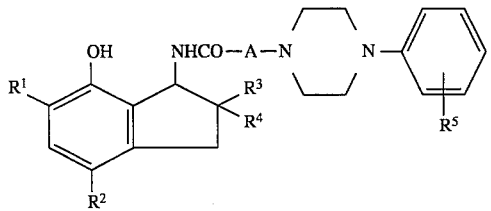

wherein $R^1$, $R^2$, $R^3$ and $R^4$ are the same or different and each is a lower alkyl group, $R^5$ is a lower alkoxy group and A is a lower alkylene group; soybean oil; yolk lecithin as an emulsifier present in said emulsion in addition to any lecithin which may be present in said soybean oil in an amount from 1 to 50 parts by weight per 100 parts by weight of said oil; glycerol as an isotonic agent; and water.

15. The oil in water fatty emulsion of claim 14, wherein the indene compound is 1-[4-(3-methoxyphenyl)-1-piperazinyl]acetylamino- 2,3-dihydro-7-hydroxy-2,2,4,6-tetramethyl-1H-indene.

16. The oil in water fatty emulsion of claim 14, wherein the amount of soybean oil is from 0.1 to 50 w/v % based on the amount of the fatty emulsion.

17. The oil in water fatty emulsion of claim 16, wherein the amount of the soybean oil is from 5 to 25 w/v % based on the amount of the fatty emulsion.

18. The oil in water fatty emulsion of claim 14, wherein the yolk lecithin is used in an amount of from 5 to 25 parts by weight per 100 parts by weight of the oil.

19. The oil in water fatty emulsion of claim 14, wherein the indene compound as the active ingredient is present in an amount of from 2 parts by weight or less per 100 parts by weight of the oil.

20. The oil in water fatty emulsion of claim 14 containing particle size diameters of 2 μm or smaller.

* * * * *